United States Patent
Eberle

(10) Patent No.: US 10,751,886 B2
(45) Date of Patent: Aug. 25, 2020

(54) GRIPPER GRIPPER FOR TRANSLATIONALLY MOVING AND ROTATING A LABORATORY VESSEL

(71) Applicant: ANDREAS HETTICH GMBH & CO. KG, Tuttlingen (DE)

(72) Inventor: Klaus-Guenter Eberle, Tuttlingen (DE)

(73) Assignee: ANDREAS HETTICH GMBH & CO. KG, Tuttlingen (DE)

( * ) Notice: Subject to any disclaimer, the term of this patent is extended or adjusted under 35 U.S.C. 154(b) by 73 days.

(21) Appl. No.: 16/303,633

(22) PCT Filed: May 22, 2017

(86) PCT No.: PCT/EP2017/062275
§ 371 (c)(1),
(2) Date: Nov. 20, 2018

(87) PCT Pub. No.: WO2017/198875
PCT Pub. Date: Nov. 23, 2017

(65) Prior Publication Data
US 2020/0094419 A1   Mar. 26, 2020

(30) Foreign Application Priority Data

May 20, 2016   (DE) .......................... 10 2016 109 317

(51) Int. Cl.
*B25J 15/02* (2006.01)
*B25J 9/04* (2006.01)
(Continued)

(52) U.S. Cl.
CPC ............. *B25J 15/026* (2013.01); *B25J 9/042* (2013.01); *B25J 15/08* (2013.01); *C12M 23/50* (2013.01); *G01N 35/0099* (2013.01)

(58) Field of Classification Search
CPC ... B25J 15/10; B25J 15/08; B25J 9/042; B25J 15/026; C12M 23/50; G01N 15/0099
(Continued)

(56) References Cited

U.S. PATENT DOCUMENTS 3,937,514 A * 2/1976 Langowski ............. E21B 19/14
  294/194
4,484,775 A * 11/1984 Norkus ................ B25J 15/0206
  269/228
(Continued)

FOREIGN PATENT DOCUMENTS

DE   3504233   11/1986
DE   10247731   4/2004
(Continued)

OTHER PUBLICATIONS

German Patent and Trademark Office, Search Report, Feb. 8, 2017, pp. 1-10, Application No. 102016109317.3, Applicant: Andreas Hettich GmbH & Co. KG.
(Continued)

*Primary Examiner* — Paul T Chin
(74) *Attorney, Agent, or Firm* — Woodling, Krost and Rust

(57) ABSTRACT

A gripping device (10) for gripping, translationally moving, and rotating a laboratory vessel (40) for samples, microorganisms or cell cultures. A support unit (12), a bearing body (14), and a gripper (16) that is rotatably mounted in the bearing body (14) are employed. The gripper (16) has a rotating body (34), in which gripping fingers (36, 38) are arranged, at least one of which is pivotably mounted in the rotating body (34). The rotating body (34) interacts with a rotary drive (30) for the rotational movement relative to the bearing body (14). The bearing body (14) is mounted in the support unit (12) in a translationally movable manner and interacts with a movement drive for the translational move- (Continued)

ment of the bearing body (14) with the rotating body with respect to the support unit (12).

23 Claims, 4 Drawing Sheets

(51) Int. Cl.
*B25J 15/08* (2006.01)
*C12M 1/00* (2006.01)
*G01N 35/00* (2006.01)

(58) Field of Classification Search
USPC .................................. 294/198, 106; 414/408
See application file for complete search history.

(56) References Cited

U.S. PATENT DOCUMENTS

| | | | | |
|---|---|---|---|---|
| 4,596,415 A | * | 6/1986 | Blatt ........................ | B25J 15/04 |
| | | | | 294/106 |
| 4,709,803 A | * | 12/1987 | Swiderski ........... | B29C 49/4205 |
| | | | | 198/468.2 |
| 5,700,046 A | | 12/1997 | Van Doren et al. | |
| 6,190,103 B1 | * | 2/2001 | Erez .................. | H01L 21/67201 |
| | | | | 294/106 |
| 6,217,094 B1 | * | 4/2001 | Hanaduka .............. | B25J 13/088 |
| | | | | 294/106 |
| 6,264,419 B1 | | 7/2001 | Schinzel | |
| 6,918,735 B2 | * | 7/2005 | Urban ............... | H01L 21/68707 |
| | | | | 294/106 |
| 7,604,584 B1 | * | 10/2009 | Wu ....................... | B23Q 3/1554 |
| | | | | 294/106 |
| 8,246,027 B2 | * | 8/2012 | Li .......................... | B25J 15/026 |
| | | | | 269/225 |
| 8,377,396 B2 | | 2/2013 | Meinicke et al. | |
| 8,414,043 B2 | * | 4/2013 | Albin .................. | B25J 15/0213 |
| | | | | 294/106 |
| 10,434,662 B2 | * | 10/2019 | Jalenques .............. | B25J 15/022 |
| 2010/0164243 A1 | * | 7/2010 | Albin ...................... | B66F 9/065 |
| | | | | 294/106 |
| 2012/0251275 A1 | | 10/2012 | Malin | |
| 2014/0377038 A1 | | 12/2014 | Malin | |
| 2015/0108780 A1 | * | 4/2015 | Gatley ................. | B25J 15/0028 |
| | | | | 294/198 |

FOREIGN PATENT DOCUMENTS

| | | |
|---|---|---|
| EP | 0995555 | 10/1998 |
| JP | H04240080 | 8/1992 |
| JP | 2000326276 | 11/2000 |

OTHER PUBLICATIONS

European Patent Office, IWritten Opinion, dated Nov. 23, 2017, pp. 1-8, Application No. PCT. EP2017/062275, Applicant: Andreas Hettich GmbH & Co. KG.

The International Bureau of WIPO English Translation of the International Preliminary Report on Patentability, dated Nov. 20, 2018, pp. 1-12, International Application No. PCT/EP2017/062275, Applicant: Andreas Hettich GmbH & Co. KG.

* cited by examiner

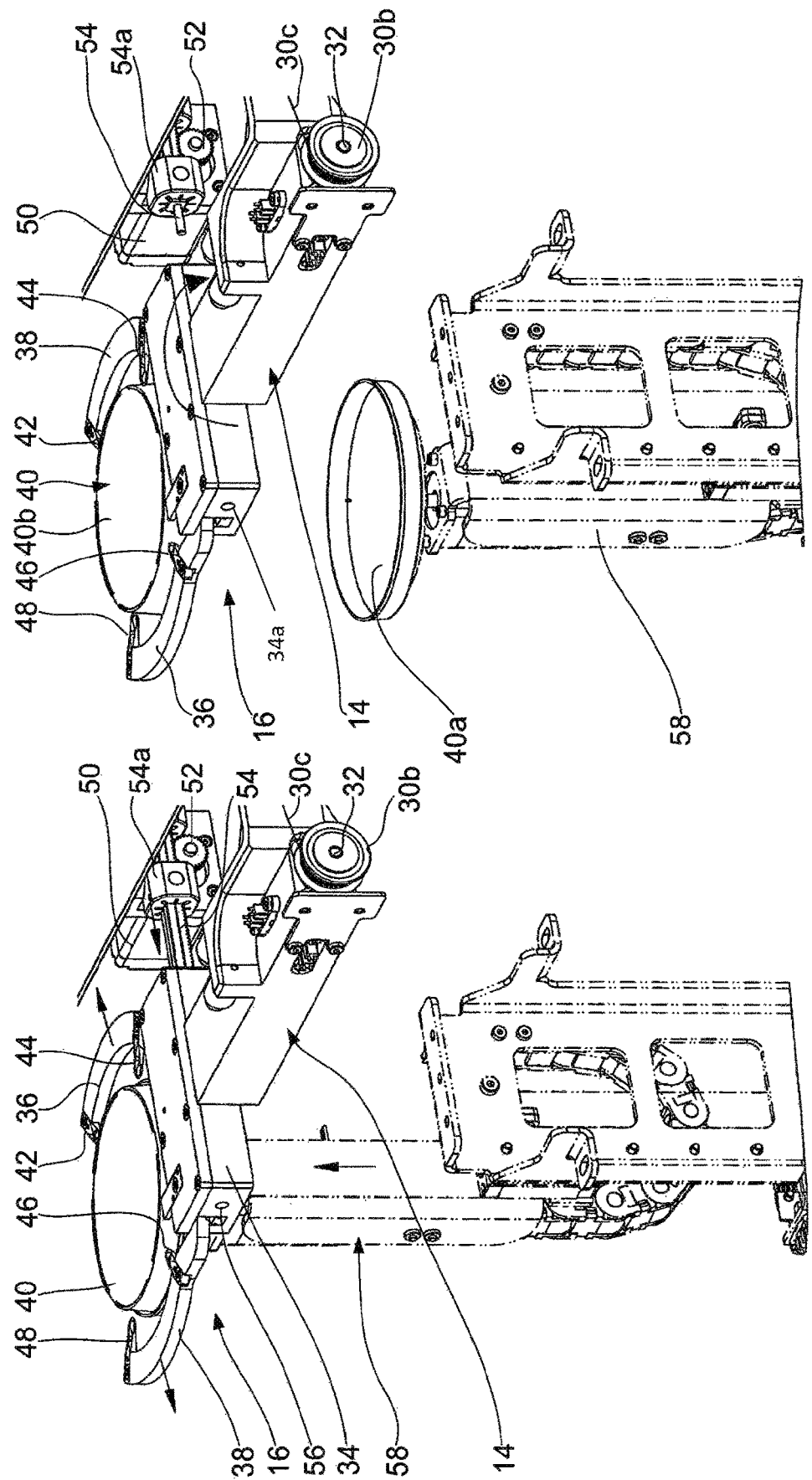

GRIPPER GRIPPER FOR TRANSLATIONALLY MOVING AND ROTATING A LABORATORY VESSEL

This patent application is the national phase entry of PCT/EP2017/062275. PCT/EP2017/062275, international application filing date May 22, 2017, claims the benefit and priority of and to German patent application no 10 2016 109 317.3, filed May 20, 2016.

PCT/EP2017/062275, international application filing date May 22, 2017, claims the benefit and priority of and to German patent application no 10 2016 109 317.3, filed May 20, 2016 and both applications are incorporated herein by reference hereto in their entireties.

The invention relates to a gripping device, in particular for gripping, translationally moving, and rotating a laboratory vessel.

In laboratories, various types of laboratory vessels are used for storing and for analyzing samples, microorganisms, cell cultures or the like. Petri dishes are particularly frequently used for this purpose. Petri dishes are available in different sizes and can be stacked and stored easily.

Petri dishes are often stored in stacks such that the lid is at the bottom and the container at the top, with the open side of the container facing downwards. One advantage, amongst others, of this orientation is that it prevents the collection of condensation on the culture medium in the container. For analyzing or treating the samples contained in the Petri dishes, the latter are often inserted in stacks into a magazine of a respective processing device and then individually moved to the analysis and/or treatment unit within the device where they will eventually be turned for processing in such a way that the open side of each container faces upwards.

For moving the Petri dishes within the processing device, a gripping device is usually provided which allows the Petri dishes to be gripped, and moved translationally as well as rotated. The gripper device has a bearing body and a gripper that is rotatably mounted within said bearing body, which gripper in turn has a rotating body in which gripping fingers are arranged. At least one of the gripping fingers is pivotably mounted. The rotating body interacts with a rotary drive for the rotational movement relative to the bearing body, and the bearing body interacts with a movement drive for translationally moving the bearing body with the rotating body with respect to the support unit. Furthermore, a gripping finger drive is provided for pivoting or moving at least one gripping finger relative to the rotating body from an open position into a gripping position, and vice versa. The gripping finger drive interacts with the gripping fingers. A drive of this type is for example known from US 2014/0377038 A1.

In practice, what frequently turns out a problem is that conventional gripper devices wear down fast, owing to their relatively high weight and the high number of moving parts. Moreover, they are difficult to replace in case of wear or after damage. Furthermore, the high masses moved have a detrimental effect on the precision of the movement of the individual parts of the gripper device.

A gripping arm for handling equipment is known from DE 35 04 233 A1. In this case, the problem is solved in that the drive motor is arranged remote from the gripper, and the drive of the gripping fingers is effected via a corresponding gear unit. A similar solution is also known from EP 0 995 555 A1.

Disclosed in DE 102 47 731 A is an automatic gripper whose gripping tool can be coupled with a drive.

It is the object of the invention to create a gripping device that performs precise movements, which, more particularly, is durable and which can be replaced quickly and easily, if necessary, while avoiding the abovementioned disadvantages.

The invention is based on the insight that the precision of the gripping device can be increased by making the parts decisive for the orientation, namely the gripper, as lightweight as possible, and this can be achieved by arranging part of the gripper drive outside the actual gripper, with the result that it will remain at the starting point during operation and be decoupled from the other part of the gripper drive, while, after gripping, the gripper moves together with the laboratory vessel and rotates it. This also facilitates the replacement of parts in case of wear.

The invention relates to a gripping device, in particular for gripping, translationally moving, and rotating a laboratory vessel for samples, microorganisms, cell cultures, or the like. The gripping device comprises a support unit, a bearing body, and a gripper that is rotatably mounted in the bearing body and has a rotating body and gripping fingers. The gripping fingers are arranged in the rotating body, and at least one of the gripping fingers is pivotably mounted in the rotating body. The rotating body interacts with a rotary drive for the rotational movement relative to the bearing body. The bearing body is mounted in the support unit in a translationally movable manner and interacts with a movement drive for the translational movement of the bearing body with the rotating body with respect to the support unit. The gripping fingers interact with a gripping finger drive for pivoting at least one gripping finger relative to the rotating body from an open position into a gripping position, and vice versa. At least one first part of the gripping finger drive for pivoting the gripper finger is arranged outside the rotating body. A second part of the gripping finger drive is arranged in the rotating body, and only in the gripping position can the first part of the gripping finger drive be connected to the second part of the gripping finger drive, otherwise, the two parts of the gripping finger drive are separated from one another. This makes the gripper lighter in weight and less complex in design, and it can therefore be moved and guided more precisely using simpler means. This reduces wear and tear, therefore also clearly lowering the costs for the gripper device. The gripper is thus more compact with regard to its overall height, and it can be inserted more easily into a measuring unit that may be sensitive to extraneous light.

Preferably, at least the first part of the gripping finger drive is arranged in the support unit. As a result, the dimensions of the gripping device can be kept compact, the gripper is lighter in weight and can be moved more precisely using simpler means. This extends the range of application of the gripping device. The support unit is not moved. The masses moved in the overall device during operation are thus reduced.

In one embodiment of the invention, the first part of the gripping finger drive is formed by a motor drive and the second part is constituted by a gear unit. This is a simple way of separating the heavy components of the drive from the moving parts, and the masses moved in operation are reduced.

To enable precise movement, the first part includes an electric motor, in particular a stepper motor.

Above all, the electric motor can interact with an actuating element associated with the gear unit, in which case the electric motor drives the gear unit via the actuating element and in this way moves at least one gripping finger. The actuating element and a respective engagement portion for the actuating element of the gear unit constitute a coupling device so that the first part and the second part can be coupled together in the gripping position. The length and the design of the actuating element can easily be adapted to the structural conditions. Use of the stepper motor allows the gripping fingers to be controlled precisely for gripping Petri dishes of different sizes. This makes the gripping device safer and more flexible in use.

More specifically, a gear unit is interconnected between the actuating element and the electric motor, which gear unit converts the rotary motion of the electric motor into a translational movement. As a result, the gripper can be of a compact design and can easily be made to move in a precise and targeted manner.

In yet another aspect of the invention, the rotating body has a receiving means which can be engaged by the actuating element. The gear unit connects to this receiving means in the rotating body in such a way that the movement of insertion of the actuating element will drive the gear unit and thus move the gripping fingers. The actuating element comes into contact with an engagement portion in a starting position of the gear unit, and as it moves further, the gear unit and ultimately the gripper fingers are moved into a position in which they grip the laboratory vessels. This allows a simple transmission of force from outside the gripper via the actuating element, without having to arrange the motor part within the gripper. In this case, the receiving means also serves as a guide for the actuating element, thus facilitating the insertion of the actuating element for a transmission of force to the gear unit. Inserting the actuating element will cause at least one gripping finger to open.

In order to enable the gripping fingers to close without additional force transmission from the outside, closing springs act on the gripping fingers in the closing direction. This ensures that also the laboratory vessels gripped by the gripping fingers will be held securely by the spring force acting on the gripping fingers and will not loosen accidentally. This danger exists in particular in the event of power loss or damage to a gear unit component. As a result, the safety of the gripping device is improved considerably. Once the laboratory vessel has been deposited or gripped by means of a slight opening movement, the gripping fingers will automatically close once the actuating element has been removed from the receiving means again, and the gear unit returns to a starting position thereof.

In one aspect of the invention, the bearing body comprises the drive for the rotational movement of the rotating body. This further decreases the weight and the mass of the gripper that comprises the rotating body and the gripping fingers, i.e. the masses moved, which in turn further reduces wear and tear of the gripper. This cuts back on the operating costs of the gripping device. In addition, this creates the conditions for precise targeted movements of the gripper within a narrow tolerance range.

It is furthermore expedient to provide two gripping fingers, with both fingers being pivotably or translationally slidably mounted in the rotating body and being connected to the gear unit of the second part of the gripping finger drive in such a manner that both gripping fingers move synchronously and in opposite directions during opening and closing. This ensures that the laboratory vessel will be centrally gripped. If the gripper and the laboratory vessel are precisely aligned relative to each other, there will be no translational movement when the laboratory vessel is gripped by the gripping fingers of the gripper.

Preferably, the gripping finger comprises a drive section which interacts with the gear unit of the drive. In this case, the drive section of the gripping finger can be disposed on the side remote from the free end and include a toothed portion which meshes with a gear of the gear unit. For one thing, gear connections of this type can be controlled very precisely, which increases the precision of the gripping device. Moreover, wear is very low which in turn improves safety and reduces operating costs.

More specifically, the gripping finger is pivotably mounted about a pivot axis. The gripping finger extends essentially in a gripper plane which is parallel to the pivot plane of the gripping finger. In this case, the pivot axis can essentially be disposed between a finger portion and the drive section, and the drive section can be disposed completely within the rotating housing. This results in a compact design and a simpler drive for moving the gripping fingers.

In one embodiment of the invention, each gripping finger has a drive section, the toothing portions of the gripping fingers are arranged opposite each other, and a gearwheel of the gear unit component meshes with the respective toothing portion of the gripping fingers. This is a simple way of ensuring that the gripping fingers will move uniformly and synchronously in opposite directions, which movement can be achieved with high precision as a function of the manufacturing quality of the tooth connection. In a preferred embodiment, the portion of the gripping fingers which grips the laboratory vessel is adapted to the shape of the outer area of the laboratory vessel. This reduces the danger of the laboratory vessel slipping out of the gripper during movement. This further improves the safety of the gripping device.

In an advantageous embodiment of the invention, retaining fingers are provided on the gripping fingers in the direction of the laboratory vessel to be gripped, which retaining fingers are disposed at a predetermined distance and a predetermined orientation from each other. As a result, the laboratory vessel, e.g. a Petri dish, will be fixed in position not only by the pressure exerted by the gripping fingers on its outer perimeter, but also by bearings in which the Petri dish is held. This is a precaution against the laboratory vessel accidentally loosening during operation of the gripping device.

Furthermore, it is very advantageous if, in the gripping position, each retaining finger of the one gripping finger is arranged diametrically opposite a retaining finger of the other gripping finger in such a way that the longitudinal axes of these two retaining fingers will be on the same axis. This improves the safety of the device in that it will prevent a laboratory vessel from slipping out of the gripping device even if the latter was inserted obliquely, i.e. not parallel to the plane of the gripper.

In one embodiment of the invention, it has turned out to be advantageous for a gripping finger to have two retaining fingers each. In the gripping position, the longitudinal axes of two opposite retaining fingers form an axis each, and the two axes are at an angle of 90° relative to each other. This arrangement of the retaining fingers is a maximum safeguard against the Petri dish slipping out of the gripping device.

Preferably, the retaining fingers have a plurality of outer surfaces which extend at an obtuse angle relative to the plane of the gripper. This prevents reflections of ambient light which, in particular, might have an adverse effect on the analysis of the contents of the laboratory vessel. In order to reduce these reflections even further, the retaining fingers can be black, or matt and a dark color.

In an alternative embodiment, the drive of the bearing body has a rail guide which is mounted in the support unit and on which the bearing body can be displaced via a translational movement. This rail guide ensures that the gripper can be displaced reliably in a manner that can be repeated precisely as often as required, thus improving the precision and service life of the overall gripping device.

Additional advantages, features and possible applications of the present invention may be gathered from the description which follows, in which reference is made to the embodiments illustrated in the drawings.

Throughout the description, the claims and the drawings, those terms and associated reference characters are used as are listed in the List of Reference Characters below. In the drawings, FIG. 1 is a three-dimensional view of a gripping device according to the invention as seen from the front at an angle from above, after it has gripped a Petri dish;

FIG. 3 is a three-dimensional detail view of the gripping device as seen from the rear at an angle from above, with a lift drive for moving the Petri dish vertically, in the position in which a container of the Petri dish is gripped, with the container not having been gripped yet in this view;

FIG. 4 is a three-dimensional detail view of the gripper device of FIG. 3, in which the lift drive has been moved into a bottom position and the container of the Petri dish has been gripped;

Figure 1:
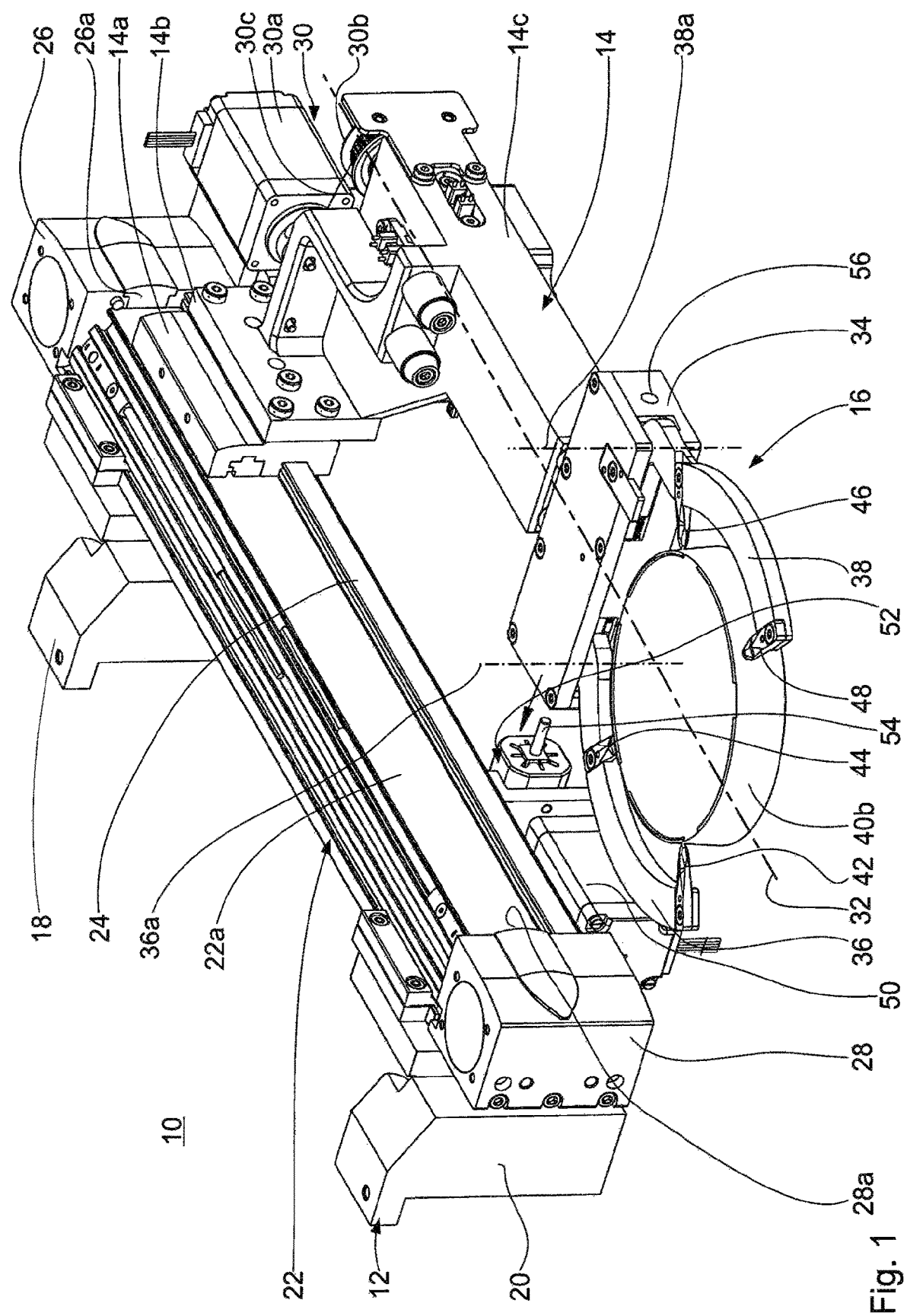
Figure 2:
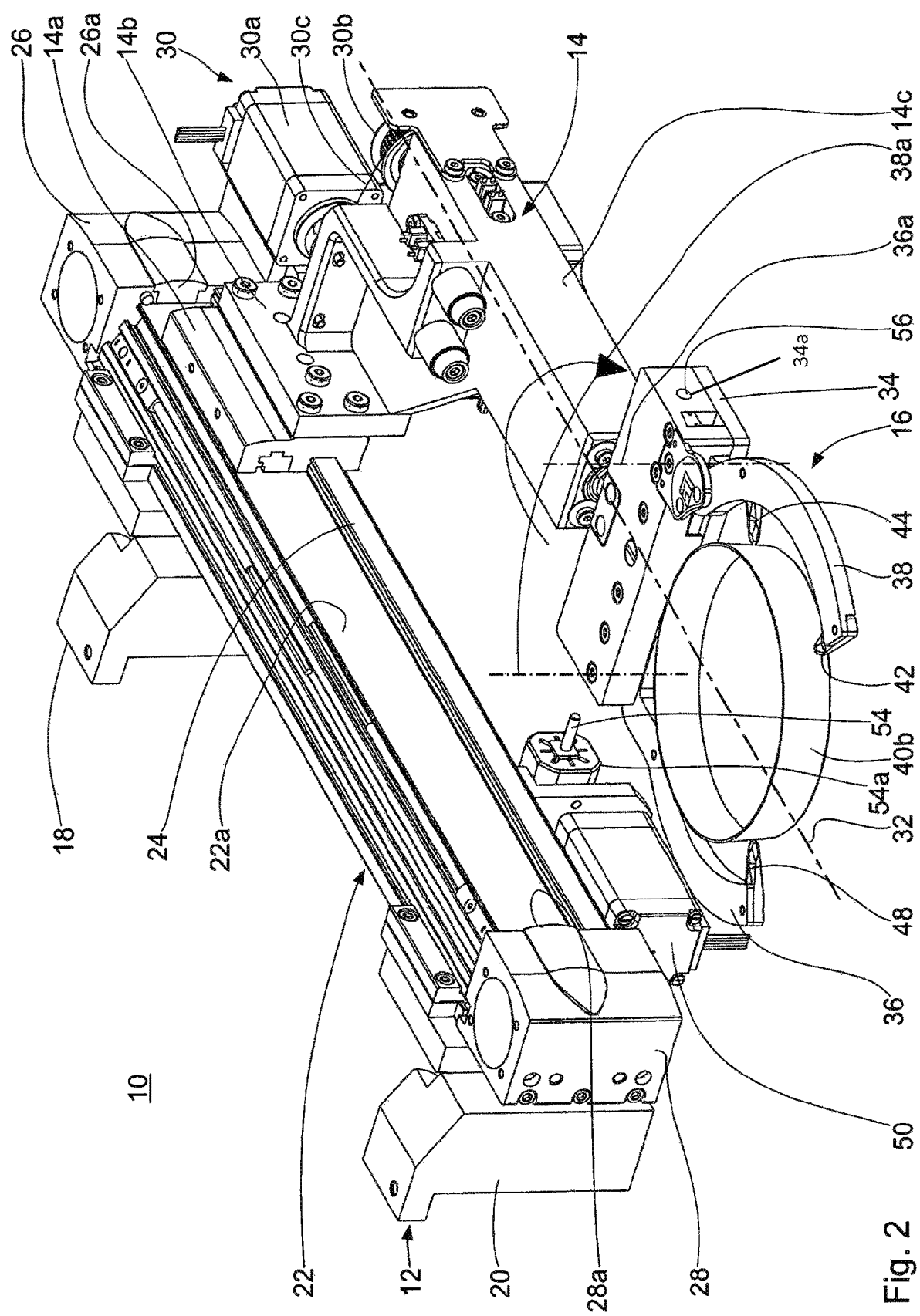
FIG. 2 is a three-dimensional view of the gripping device of FIG. 1, in which the gripped Petri dish has been rotated by 180°.

FIG. 1 is a three-dimensional view of a gripping device 10 comprising a support unit 12, a bearing body 14 and a gripper 16. FIG. 2 is a similar view but with the gripper 16 and the bearing body 14 rotated by 180°.

The support unit 12 has two supports 18 and 20 which can be connected to a housing or a support rack not shown here. Extending between the supports 18, 20 is a rail 22 on which the bearing body 14 is mounted for its translational movement thereon. For this purpose, a foot 14a of the bearing body 14 positively engages a support rail 24 which extends parallel to the rail 22 and is disposed on a lateral surface 22a of the rail 22. As seen in FIG. 1, the lateral surface 22a extends above the support rail 24, which surface 22a likewise forms a contact and sliding surface for the bearing body 14. Part of the bearing body 14 makes contact with the lateral surface 22a and slides along this lateral surface 22a when it is moved translationally.

Drive blocks 26, 28 are provided at the ends of the rail 22, in which a motor and deflection pulleys for a drive cable—alternatively a drive belt—are mounted. The drive cable has its each of its ends connected to the foot 14a of the bearing body 14, extends into the drive blocks 26, 28 and, via the deflection pulley mounted there, out of the drive blocks 26, 28 again inside the rail 22. The bearing blocks 26, 28 each have stops 26a, 28a which are associated with a foot 14a of the bearing body 14. For the sake of clarity, the drive cable is not shown. The deflection pulleys and the motor, which drives an associated deflection pulley, are mounted inside the bearing block 26, and another deflection pulley is located inside the bearing block 28. This deflection pulley is not driven but only rotatably mounted. The deflection pulleys and the motor are not shown in the Figures.

The foot 14a has a base plate 14b screwed onto it, which base plate 14b in turn has an angular body 14c mounted on it. However, the base plate 14b and the angular body 14c can also be designed in one piece as a continuous part. The angular body 14c initially extends away from the rail 22, at right angles relative to the base plate 14b, and then parallel to the support unit 12. As seen in FIGS. 1 and 2, the angular body 14c extends parallel to the direction from drive block 26 to drive block 28. At the free end of the angular body 14c, the gripper 16 engages in the angular body 14c, is rotatably mounted there and connected to a rotary drive 30. The rotary drive 30 consists of an electric drive motor 30a and a multi-turn gearbox which are both arranged at the end of the angular body 14c remote from the gripper 16. The multi-turn gearbox comprises a drive roller 30b which is concentric relative to the rotational axis 32 of the gripper 16 and connected to the gripper 16, said roller 30b being connected to a motor shaft of the drive motor 30a via a drive belt 30c that is merely indicated in the drawing. The rotary drive 30 is used to turn the gripper 16 about the rotational axis 32 if required, preferably by 180°.

The gripper 16 consists of the rotating body 34 which engages in the angular body 14c, which body 34 is essentially rectangular in shape. Mounted in the rotating body 34 are two gripping fingers 36 and 38 and a gear unit 34a, which gripping fingers 36 and 38 can each be pivoted synchronously in opposite directions about a pivot axis 36a, 38a. As an alternative, these are mounted in the rotating body 34 so as to be translationally movable. The pivot axes 36a and 38a extend at right angles to a gripper plane which is defined by the gripping fingers 36 and 38. The pivot axes 36a and 38a share the respective gripping finger 36 or 38 in a finger section as well as a drive section which has a toothed portion and meshes with a gearwheel or a gear rack of the gear unit 34a within the rotating body 32. The finger section is arranged outside the rotating body 32, is curved to fit the shape of the laboratory vessel to be gripped, which is in the form of a Petri dish, and has two retaining fingers 42, 44 each on the one side and two retaining fingers 46 and 48 each on the other side.

The retaining fingers 42 and 46 as well as 44 and 48 are arranged diametrically opposite each other. The retaining fingers 42 to 48 are oriented and arranged such that the longitudinal axes of the retaining fingers 42 and 46 on the one side are identical to the longitudinal axes of the retaining fingers 44 and 48 on the other side. The longitudinal axis of the retaining fingers 42 and 46 and the longitudinal axis of the retaining fingers 44 and 48 are offset by 90° in relation to each other. Alternatively, the fingers can also be aligned parallel to each other.

Arranged underneath the rail 22 is an electric stepper motor 50 which interacts with a gear unit 52. The gear unit 52 is operatively connected to an actuating element 54 in the form of a rack. The stepper motor 50 and the gear unit 52 are used to move the actuating element 54 outwards and back again in a predetermined manner. The motor 50, the gear unit and the actuating element 54 form the first part of a drive for the gripping fingers 36, 38. Associated with the actuating element 54 is a receiving means 56 in the bearing body 14 of the gripper 16 which serves as an entrance and guide for the actuating element 54. The gear unit 34a (not shown in detail here) connects to the receiving means 56 and converts the translational movement of the actuating element 54 into pivot movements in opposite directions of the gripping fingers 36, 38. This gear unit 34a which is mounted in the rotating body 34 essentially consists of a gear rack driven by the actuating element 54, a gearwheel which meshes with the gear rack and which interacts with the drive section of the respective gripping finger 36 or 38. The drive section is essentially formed by a toothing area which engages in the gearwheel and is shaped in such a way that each turn of the gearwheel will cause a pivotal movement of the gripping finger 36 and 38.

A receiving means 56 is provided on either side of the bearing body 34, so that, regardless of the rotational position of the gripper 16, when the receiving means 56 of the bearing body 34 has been appropriately aligned, via a translational movement, relative to the actuating element 54, the actuating element 54 will be able to open the gripping fingers 36, 38 as it moves into the receiving means 56 and the adjoining gear unit. As an alternative, the receiving means 56 can also be provided on a side of the bearing body 34. The gripping fingers 36, 38 are preloaded to their closed position by springs. As the actuating element 54 is retracted, the spring force of the springs will act on the gripping fingers 36, 38, causing the latter to move into their closed position and, if a Petri dish 40 is present, into a gripping position.

Figure 5:
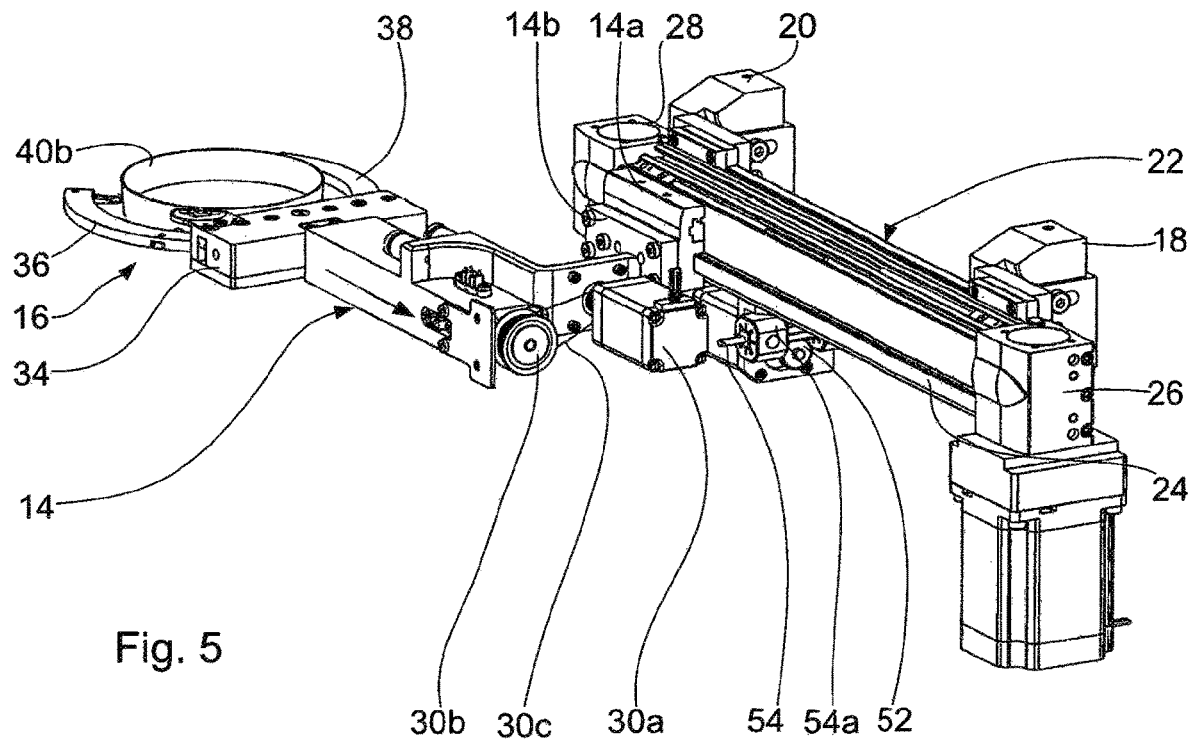
FIG. 5 is a three-dimensional view of the gripping device of FIG. 4 but in a translationally moved position without a lift drive, with the Petri dish rotated in the area of the analysis device.
Figure 6:
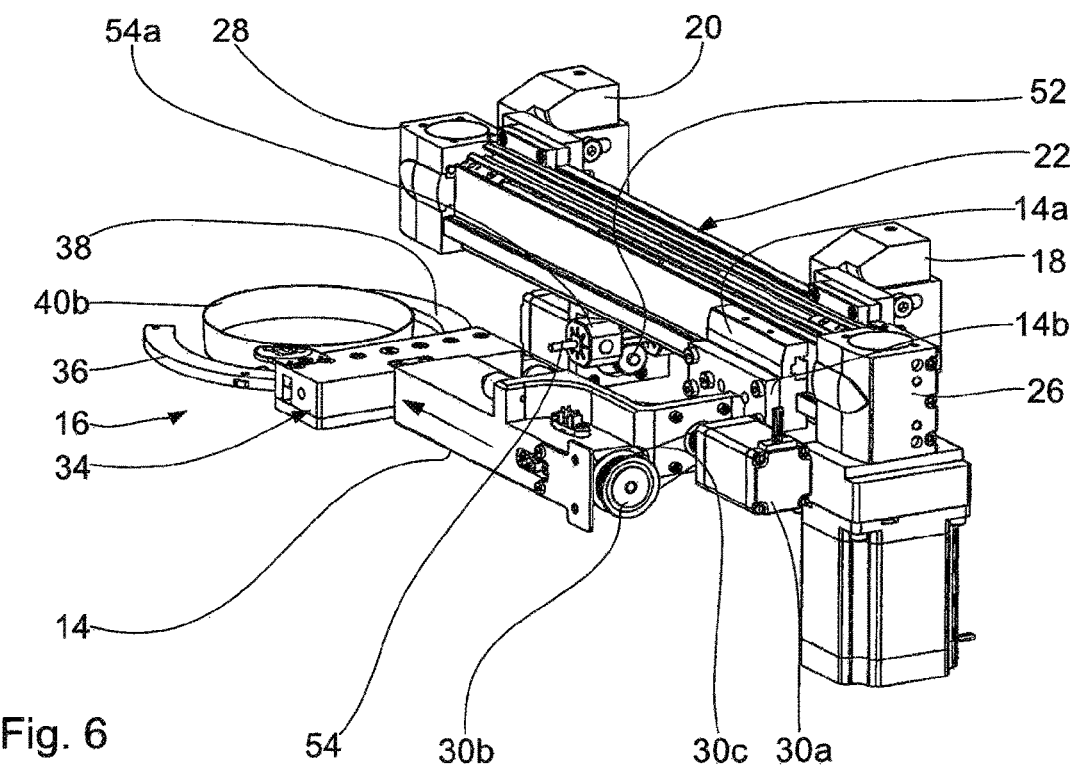
FIG. 6 is a three-dimensional view of the gripping device according to the invention as seen from the rear at an angle from above, before it is translationally moved into the area of an analysis device.

As seen in FIG. 4, the Petri dish consists of a container 40b and a lid 40a. As seen in FIG. 1, the container 40b has been gripped by the gripping fingers 36, 38 and is open to the bottom. In the view of FIG. 2, the container 40b has been rotated by 180°. In FIG. 3, the Petri dish 40 consisting of container 40b and lid 40a is still closed, with the container 40b at the top and the lid 40a at the bottom in this view. Underneath the Petri dish 40, a lifting device 58 is provided which moves the Petri dish 40 vertically from a pickup position to a position in which the container 40b can be gripped by the gripper 16. This position is shown in FIG. 3. Before the Petri dish 40 is moved into this position by the lifting device 58, the actuating element 54 moves into the receiving means 56, actuates the gear unit arranged in the bearing body 34 and thus causes the gripping fingers 36, 38 to open. This causes the first and second parts of the gripping finger drive to be coupled to each other. The lifting device 58 now moves the Petri dish 40 upwards into a predetermined position in which the container 40b of the Petri dish 40 is gripped by the gripping fingers 36, 38 via the retaining fingers 42 to 48. For this purpose, the actuating element 54 returns to its starting position, the spring force causes the gripping fingers 36, 38 to close, and the container 40b of the Petri dish 40 is gripped. This causes the first and second parts of the gripping finger drive to be decoupled from each other again. Next, the lifting device 58 together with the lid 40a moves downward to such an extent that the gripper 16 can be rotated by 180°. This position is shown in FIGS. 2 and 5. The two parts of the gripping finger drive are thus only connected to each other in the gripping position, and in particular even here for the sole purpose of gripping the Petri dish 40. Otherwise, the two parts are separated from one another.

Subsequently, the bearing body 14, together with the gripper 16 and the container 40b of the Petri dish 40, is translationally moved into a position underneath the analysis device (see FIG. 5) that is not shown, however, for the sake of clarity. In this position, the culture contained in the container 40b is then analyzed using imaging methods. Subsequently, the bearing body 14 with the gripper 16 returns to its previous position, the gripper 16 rotates the container 40b by 180°, the lifting device 58 with the lid 40a of the Petri dish travels upwards until the container 40b engages the lid. The gripper 16 is now in its gripping position again, and the first and second parts of the gripping finger drive are coupled to one another in that the actuating element 54, which is guided by a guide 54a, in which the rotational movement of the stepper motor 50 is converted into a translational movement of the actuating element 54 by the gear unit 54b, enters the receiving unit 56 again and thus causes the gripping fingers 36, 38 to open, which in turn releases the Petri dish 40 and causes the lifting device 58 to move the Petri dish 40 downward for further transport.

The retaining fingers 42 to 48 have a plurality of individual outer surfaces at an angle to each other, which are aligned at an obtuse angle to the gripper plane. This creates a so-called stealth shape which prevents the creation of interfering reflections during the image processing analysis. In addition, the fingers are also black or of a dark color.

The invention is characterized in that the first part of the gripping finger drive for opening the gripping fingers 36, 38 is arranged outside the moving parts and will only be coupled to the second part of the gripping finger drive in the gripping position, for the actual gripping step. This creates the prerequisites to ensure that the moving masses of the gripping device are smaller in operation, thus enabling more precise gripping and moving. Moreover, this makes for a very compact system as regards its overall height.

LIST OF REFERENCE SIGNS

10 gripping device
12 support unit
14 bearing body
14a foot
14b base plate
14c angular body
16 gripper
18 support
20 support
22 rail
22a side surface
24 support rail
26 drive block
26a stop
28 drive block
28a stop
30 rotary drive
30a drive motor
30b drive roller
30c drive belt
32 rotational axis
34 rotating body
34a gear unit—second part of gripping finger drive
36 gripping finger
36a pivot axis
38 gripping finger
38a pivot axis
40 Petri dish
40a Petri dish lid
40b Petri dish container
42 retaining finger
44 retaining finger
46 retaining finger
48 retaining finger
50 stepper motor
52 gear unit of the actuating element 54 drive
54 actuating element
54a actuating element guide
56 receiving means in the rotating body 34 of the gripper 16
58 lifting device

The invention claimed is:

1. Gripping device (10), for gripping, translationally moving, and rotating a laboratory vessel (40) for samples, microorganisms, or cell cultures, comprising a support unit (12), a bearing body (14), and a gripper (16) that is rotatably mounted in the bearing body (14) and has a rotating body (34) in which gripping fingers (36, 38) are arranged, at least one of which is pivotably mounted in the rotating body (34), wherein the rotating body (34) interacts with a rotary drive (30) for the rotational movement relative to the bearing body (14), the support body (14) is mounted in the support unit (12) so as to be translationally movable and interacts with a movement drive for the translational movement of the bearing body (14) with the rotating body (34) relative to the support unit (12), and the gripping fingers (36, 38) interact with a gripping finger drive (50, 52, 54) for pivoting at least one gripping finger (36, 38) relative to the rotating body (34) from an open position to a gripping position wherein at least one first part of the gripping finger drive (50, 52, 54) for pivoting the gripper fingers (36, 38) is arranged outside the rotating body (34), and a second part of the gripping finger drive (34a) is arranged in the rotating body (34), and only in the gripping position can the first part of the gripping finger drive (50, 52, 54) be connected to the second part of the gripping finger drive (52), otherwise, the two parts of the gripping finger drive (50, 52, 54) are separated from one another.

2. Gripping device according to claim 1, characterized in that at least the first part of the gripping finger drive (50, 52, 54) is arranged in the support unit (12).

3. Gripping device according to claim 1, characterized in that the first part (50, 52, 54) is provided in the form of a motor drive (50, 52, 54) and the second part is provided in the form of a gear unit (34a).

4. Gripping device according to claim 3, characterized in that the first part (50, 52, 54) comprises a stepper motor (50).

5. Gripping device according to claim 4, characterized in that the electric motor (50) interacts with an actuating element (54) associated with the gear unit (34a), wherein the electric motor (50) drives the gear unit (34a) via the actuating element (54) and moves at least one gripping finger (36, 38).

6. Gripping device according to claim 5, characterized in that a gear unit (52) is interconnected between the actuating element (54) and the electric motor (50), which gear unit (52) converts the rotational movement of the electric motor (50) into a translational movement.

7. Gripping device according to claim 6, characterized in that the rotating body (34) has a receiving means (56) which can be engaged by the actuating element (54), with the gear unit (34a) being arranged following the receiving unit (56) in the rotating body (34) in such a way that the gear unit (34a) will be driven by the insertion movement of the actuating element (54).

8. Gripping device according to claim 7, characterized in that the insertion movement of the actuating element (54) will cause at least one gripping finger (36, 38) to open.

9. Gripping device according to claim 3, characterized in that two gripping fingers (36, 38) are provided, wherein, both gripping fingers (36, 38) are mounted in the rotating body (34) so as to be pivotable or translationally movable therein and are connected to the gear unit (34a) in such a way that both gripping fingers (36, 38) will move synchronously in opposite directions during opening and closing.

10. Gripping device claim 3, characterized in that the gripping finger (36, 38) comprises a drive section which interacts with the gear unit (34a) of the drive.

11. Gripping device according to claim 10, characterized in that the drive section of the gripping finger (36, 38) is arranged on the side remote from the free end and has a toothing area which interacts with a gear wheel of the gear unit (34a).

12. Gripping device according to claim 11, characterized in that the gripping finger (36, 38) is pivotably mounted around a pivot axis (36a, 38a), that the gripping finger (36, 38) essentially extends in a gripper plane which is parallel to the pivot plane of the gripping finger (36, 38).

13. Gripping device according to claim 12, characterized in that the pivot plane (36a, 38a) is essentially located between a finger section and a drive section.

14. Gripping device according to claim 13, characterized in that the drive section is completely located in the rotary housing (34).

15. Gripping device according to claim 14, characterized in that each gripping finger (36, 38) has a drive section, that the toothing areas of the gripping fingers (36, 38) are arranged opposite each other and that a gearwheel of the gear unit (34a) meshes with the respective toothing area of the gripping fingers (36, 38).

16. Gripping device according to claim 1, characterized in that springs act on the gripping fingers (36, 38) in the closing direction, with the result that the laboratory vessels (40) gripped by the gripper (16) will be held securely owing to the spring force acting on the gripping fingers (36, 38), and will not accidentally become loose.

17. Gripping device according to claim 1, characterized in that the bearing body (14) comprises the drive (30) for the rotational movement of the rotating body (34).

18. Gripping device according to claim 1, characterized in that the gripping fingers (36, 38) are matched to the shape of the outer area of the laboratory vessel (40) in the area where the vessel is to be gripped.

19. Gripping device according to claim 1, characterized in that retaining fingers (42 to 48) facing in the direction of the laboratory vessel 840) to be gripped are provided on the gripping fingers (36, 38), which retaining fingers (42, to 48) are arranged at a predetermined distance and orientation from each other.

20. Gripping device according to claim 1, characterized in that the drive of the bearing body (14) has a rail guide (22, 24) which is mounted in the support unit (12) and which can be used for a translational movement of the bearing body (14) thereon.

21. Gripping device according to claim 19, characterized in that, in the gripping position, each retaining finger (42 to 48) of a certain gripping finger (36, 38) has a retaining finger (42 to 48) of a respective other gripping finger (36, 38) arranged diametrically opposite it in such a way that the longitudinal axes of these two retaining fingers (42 to 48) will extend in one axis.

22. Gripping device according to claim 21, characterized in that a gripping finger (36, 38) has two retaining fingers (42 to 48) each, that, in the gripping position, the longitudinal axes of two opposite retaining fingers (42 to 48) each form an axis and that the two axes are at an angle of 90° to each other.

23. Gripping device according to claim 21 characterized in that the retaining fingers (42 to 48) have a multitude of outer surfaces which are aligned at an obtuse angle relative to the gripper plane.

* * * * *

UNITED STATES PATENT AND TRADEMARK OFFICE
CERTIFICATE OF CORRECTION

PATENT NO. : 10,751,886 B2
APPLICATION NO. : 16/303633
DATED : August 25, 2020
INVENTOR(S) : Eberle It is certified that error appears in the above-identified patent and that said Letters Patent is hereby corrected as shown below:

On the Title Page

Item (54), Column 1, Line 1, after the first occurrence of "GRIPPER" delete "GRIPPER".

In the Specification

Column 1, Line 1, after the first occurrence of "GRIPPER" delete "GRIPPER".

Signed and Sealed this
Twenty-seventh Day of August, 2024

Katherine Kelly Vidal
*Director of the United States Patent and Trademark Office*